US005908630A

United States Patent [19]

Fenwick

[11] Patent Number: 5,908,630
[45] Date of Patent: Jun. 1, 1999

[54] SWINE IMMUNIZATION USING LIVE, RTX TOXIN-SECRETING ORGANISMS

[75] Inventor: Bradley W. Fenwick, Manhattan, Kans.

[73] Assignee: Kansas State University Research Foundation, Manhattan, Kans.

[21] Appl. No.: 08/541,226

[22] Filed: Oct. 12, 1995

Related U.S. Application Data

[63] Continuation-in-part of application No. 08/428,507, Apr. 25, 1995, abandoned, which is a continuation of application No. 08/242,375, May 13, 1994, abandoned.

[51] Int. Cl.$^6$ ........................ A61K 39/102; A61K 39/02; A61K 39/205; A01N 37/18
[52] U.S. Cl. ..................... 424/255.1; 424/184.1; 424/256.1; 424/257.1; 424/258.1; 424/234.1; 424/236.1; 424/825; 424/241.1; 514/2
[58] Field of Search ............................. 424/184.1, 255.1, 424/256.1, 257.1, 258.1, 234.1, 236.1, 825, 241.1; 514/2

[56] References Cited

U.S. PATENT DOCUMENTS

| | | |
|---|---|---|
| 3,364,117 | 1/1968 | Smith . |
| 3,907,987 | 9/1975 | Wilson ..................................... 424/92 |
| 3,975,517 | 8/1976 | Wilson ..................................... 424/87 |
| 4,559,306 | 12/1985 | Kucera .................................... 435/253 |
| 4,626,430 | 12/1986 | Kucera .................................... 424/92 |
| 4,681,762 | 7/1987 | Oeschger et al. ......................... 424/92 |
| 5,525,504 | 6/1996 | Goebel et al. . |
| 5,559,008 | 9/1996 | Chang . |
| 5,726,016 | 3/1998 | De Muth et al. . |

OTHER PUBLICATIONS

Pohl et al International J. Systematic Bacteriology 33:510–514, 1983.
Conlon et al, Inf. & Imm. 59(2):587–591, 1991.
Macinnes et al Ed:Gylesetal IN: Pathogenesis of Bacterial Infections In Animals.
Menestrina et al, Toxicology, 87:249–267, 1994.
Welch, Mol. Microbiology, 5 (3):521–528, 1991.
Nielsen, Nord. Vet. Med. 86: 221–234, 1984.
Czuprynski et al. 1995. Trends in Microbiol. 3(12):480–83.
Lally et al. 1994. JBC. 269(49): 31289–31295.
Jansen et al. 1995. Inf. & Imm. 63(1):27–37.
Chang et al. 1993 Inf & Imm. 61(5): 2089–95.
Forestier et al. 1991. Inf & Imm. 59(11): 4212–4220.
Tarigan et al. 1996. Australian Vet. J. 73(5):164–169.
Guthmiller et al. 1995. Microbial Pathogenesis. 18:307–321.
Kobisch et al. 1989. Vet. Rec. 124:57–61.
Ma 1991. Dissabs. Int. 52(12B):6213.
Fogrd et al. 1989. Vet. Rec. 125:7–11.
Bosse et al. 1992. Inf. & Imm. 60(2): 479–84.
Frey et al. 1993 J. Gen. Microbiol. 139:1723–28.
Fenwick et al. 1986. Inf. & Imm. 54(2): 575–82.
Lenser et al. 1988. Vet. Microbiol. 18:335–48.
Coote, Structural and Functional Relationships Among the RTX Toxin Determinants of Gram–Negative Bacteria; FEMS Microbiology Reviews 88 (1992) 137–162.
Welch, et al. The Synthesis and Function of the *Escherichia coli* Hemolysin and Related RTX Exotoxins; FEMS Microbiology Immunoloogy 105 (1992) 29–36).
Taylor, *Actinobacillus equuli* and *A. suis,* Section 4, Bacterial Diseases, pp. 634–636, 1986.
Hennessy, et al.; Serotype Identification of *Actinobacillus pleuropneumoniae* by Arbitrarily Primed Polymerase Chain Reaction; Journal of Clinical Microbiology, May 1993, pp. 1155–1159. vol. 31, No. 5.
Burrows et al.; Molecular Characterization of an RTX Toxin Determinant from *Actinobacillus suis,* Infection and Immunity, Jun. 1992, pp. 2166–2173, vol. 60, No. 6.
Frey et al.; Immunological Properties of *Actinobacillus pleuropneumoniae* Hemolysin I, Veterinary Microbiology, 28 (1991) 61–73.
Devenish et al.; Immunoserological Comparison of 104–Kilodalton Proteins Associated with Hemolysis and Cytolysis in *Actinobacillus pleuropneumoniae, Actinobacillus suis, Pasteurella haemolytica,* and *Escherichia coli,* Infection and Immunity, Oct. 1989, pp. 3210–3213, vol. 57, No. 10.

*Primary Examiner*—Nita Minnifield
*Attorney, Agent, or Firm*—Hovey,Williams, Timmons & Collins

[57] ABSTRACT

An improved method and vaccine is provided for the immunization of swine against infectious diseases caused by RTX toxin-secreting bacteria (e.g., porcine pleuropneumonia) which comprises administering to swine an effective amount of a live, immunizing, RTX toxin-secreting organism which induces in the swine a sufficiently high RTX toxin-neutralizing antibody titer to at least prevent clinical symptoms of the disease in the swine. For example, an intranasally administered, live, low virulence strain of *A. suis* (EM1) confers immunity upon swine against challenge with a virulent, disease-causing strain of *A. pleuropneunmoniae.*

13 Claims, 4 Drawing Sheets

SWINE IMMUNIZATION USING LIVE, RTX TOXIN-SECRETING ORGANISMS

RELATED APPLICATION

This is a continuation-in-part of application Ser. No. 08/428,507, filed Apr. 25, 1995, now abandoned which is a continuation of Ser. No. 08/242,375, filed May 13, 1994, now abandoned.

BACKGROUND OF THE INVENTION

1. Field of the Invention

The present invention is broadly concerned with an improved method and vaccine for the immunization of swine against infectious diseases caused by bacteria which secrete RTX toxins, such as pleuropneumonia, pneumonia, enteritis, septicemia and rhinitis sore particularly, the invention pertains to such a method and vaccine which includes an effective amount of a live, immunizing, RTX toxin-secreting organism which induces in the swine a sufficiently high RTX toxin-neutralizing antibody titer to at least prevent clinical symptoms of the diseases.

2. Description of the Prior Art

A number of gram-negative bacteria are known to secrete RTX toxins in swine. Such bacteria are generally selected from the group consisting of the genera Actinobacillus, Pasteurella, Haemophilus, Escherichia and Salmonella. The RTX toxins are a family of calcium-dependent, pore-forming, secreted toxins.

Organisms which secrete RTX toxins are known to cause a variety of debilitating swine diseases such as pleuropneumoniae pneumonia, enteritise septicemia and rhinitis. These diseases, and particularly porcine pleuropneumonia, have very serious economic consequences for pig farmers. Susceptible pigs exposed to aerosolized *A. pleuropneumoniae* develop acute necrotic bronchopneumonia following inhalation of a threshold number of organisms. The toxins produced by *A. pleuropneumoniae* and the associated inflammatory response rapidly induce focal vascular necrosis leading to localized thrombosis, edema, ischemic necrosis, and fibrinous pleuritis. The severity of the diseases following exposure to *A. pleuropneumoniae* is dependent on the relative virulence of the strain involved and the number of organisms inhaled. In a typical pleuropneumonia outbreak caused by a virulent strain of *A. pleuropneumoniae*, morbidity may be in excess of 50% with mortality being quite variable, from 1–10%. Growing pigs are often most severely affected, although immunologically susceptible sows, boars and piglets may also develop severe disease. A full discussion of the causes, epidemiology and treatment of pleuropneumonia is set forth in Fenwick et al., Porcine Pleuropneumonia: An Update, *J. Am. Vet. Ned. Assoc.*, 1994; 204:334, which is incorporated by reference herein.

While the impact of porcine pleuropneumonia and other diseases caused by bacteria which secrete RTX toxins is well known, there have heretofore been no commercially available vaccines with the ability to reliably induce protective immunity against these diseases. Some vaccines reduce mortality rates, but none are effective in preventing infections of *A. pleuropneumoniae* or apparently the development of carrier pigs capable of shedding the organism. Additionally, difficulties with antigens and adjuvants have led to injection site lesions. As far as is known, none of the prior vaccines induce significant neutralizing antibody titers in swine against the exotoxins such as the RTX toxins secreted by the etiologic organisms.

There is accordingly a real and unsatisfied need in the art for an improved vaccine and method whereby swine may be immunized against infectious diseases caused by bacteria which secrete RTX toxins.

SUMMARY OF THE INVENTION

The present invention overcomes the problems outlined above and provides a method and vaccine for the immunization of swine against infectious diseases caused by RTX toxin-secreting bacteria. In practice, the method of the invention involves administration to the swine of an effective amount of a live, immunizing, RTX toxin-secreting organism belonging to a species which is different than the species of said bacteria which induces in the swine a sufficiently high RTX toxin-neutralizing antibody titer to at least prevent clinical symptoms of the diseases in question. In preferred forms, the immunizing organism also induces sufficient antibody titer to prevent infection in the swine.

The immunizing organisms are normally selected from the group consisting of gram-negative bacteria of the genera Actinobacillus, Pasteurella, Haemophilus, Escherichia and Salmonella. Such organisms are normally live or modified live bacteria of relatively low virulence; accordingly, inoculated swine normally do not suffer any significant clinical disease because of the immunization In the case of swine immunization against porcine pleuropneumonia, use of an appropriate strain of *A. suis* as the live immunizing organism has been found to be particularly effective. One specific strain of *A. suis* of particular interest in this context is the EM1 strain A sample of this strain has been deposited with the American Type Culture Collection, Rockville, Md., and has been accorded Accession No. 55579.

The vaccine of the invention normally includes an appropriate immunizing organism in a suitable carrier, such as sterile saline or any other pharmaceutically acceptable carrier which will support the viability of the organism. This vaccine may be administered parenterally, orally or most advantageously intranasally to the swine Although the invention finds particular utility in the immunization of swine against pleuropneumonia, appropriate vaccines can be prepared for immunization of other endemic infectious swine diseases such as enteritis, pneumonia, septicemia and rhinitis, which are caused by bacteria which secret RTX-type toxins.

The RTX bacterial toxins, because of their ability to damage tissues and cells are important factors in the bacteria's ability to cause disease. Immunization with killed bacteria or their toxins do not induce an antibody response capable of neutralizing this effect, and thus the ability of these products to reliably prevent disease is limited. The protection that they do provide is solely dependent on the development of immunity to surface antigens, either capsule or lipopolysaccharide. In contrast, exposure to live organisms induces a toxin-neutralizing immune response and significant protection against disease. The specific mechanism by which this protection is obtained is not understood, but it is theorized that the RTX toxins are fragile as well as self-aggregating and thus do not withstand the processes associated with the production of killing bacteria or the development of toxin-based vaccines. In addition, the slow and sustained release of the toxins by the organism may provide adequate exposure of the critical portions of the toxin to the immune system.

DETAILED DESCRIPTION OF THE PREFERRED EMBODIMENTS

Figure 1:
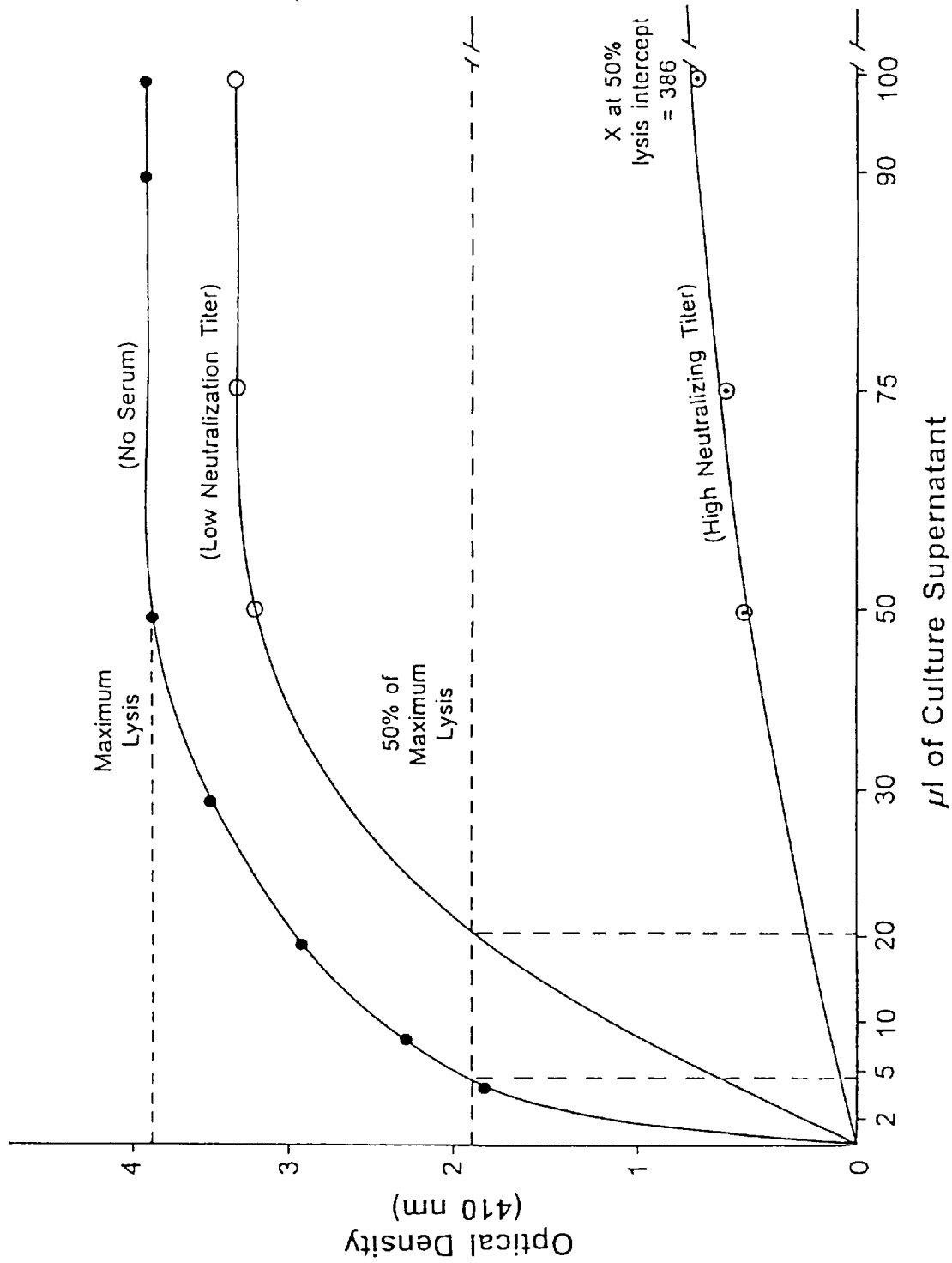
FIG. 1 depicts a graph measuring the hemolytic activity of culture supernatants and the hemolysin-neutralizing antibody titer of serum; a standard curve of the hemolytic activity of culture supernatant (No Serum) demonstrates that it takes approximately 5 μl of this supernatant to lysis 50% of the available sheep erythrocytes (5 μl =one hemolytic unit); changes in the hemolytic activity of this culture supernatant associated with the addition of 5 μl of serum with low-neutralizing and high-neutralizing ability are illustrated.

The following examples illustrate preferred embodiments of the invention and use thereof. It is to be understood, however, that this example is presented by way of illustration only and nothing therein should he taken as a limitation upon the overall scope of the invention.

EXAMPLE 1

In this example, the virulence potential of the EM1 strain of *A. suis* was evaluated, and the ability of this strain to immunize the swine against the clinical and pathological consequences of exposure to a virulent strain of *A. pleuropneumoniae* was tested.

The EM1 strain of *A. suis* was isolated from a swine herd and has been characterized as a gram-negative, nonmotileal non-spore-forming, small rod shaped bacteria that does not require X or V factor for growth. It is beta-hemolytic on sheep red blood cell agar. The strain is catalase and urease positive weakly oxidase positive, and ferments maltose, esculin, glucose, lactose, salicin, sucrose and trehalose. It is indole negative and does not ferment inulin, mannitol, raffinose, or sorbitol. DNA analysis of this strain confirmed its identity as *A. suis* and not a biotype 1 strain or other variant of *A. pleuropneumoniae*. See Hennessy et al., Serotwoe Identification of *Actinobacillus pleuropneumoniae* by Arbitrary Primed Polymerase Chain Reaction, *J. Clinical Microbiology* 31:1115–1159 (1993) and Sirois, et al., Construction of a DNA Probe and Detection of *Actinobaccilus Pleuropneumoniae* by Using Polymerase Chain React:ion, *J. Clinical Microbiology* 29:1183–1187 (1991), which are incorporated by reference herein.

Eight ten-week old pigs were obtained from a swine herd and housed in an infectious disease isolation room. Previous serologic examination of the pigs from this swine herd indicated that pigs in the herd did not have serum hemolysin neutralization titers against the type 1 hemolysin of *A. pleuropneumoniae* (an RTX-type toxin)e and that the herd was free of clinical diseases that could be attributed to *A. pleuropneumoniae*. Four days after isolation of the pigs, they were ear-tagged, blood samples were collected, and each pig was then intranasally injected with approximately 10 ml of a log phase culture of the EM1 strain of *A. suis* (approximately $10^8$ colony forming units) in sterile saline. The clinical conditions of the pigs was evaluated daily. One month later, additional blood samples were collected from the inoculated pigs.

Twenty-two days later, an additional eight control pigs were acquired from the same source. These pigs were the same age as the original EM1-inoculated pigs. The control pigs were placed in the same room as the EM1 infected pigs. Three days later, all of the pigs were challenged intranasally with 3 ml of a log phase culture of serotype 1 *A. pleuropneumoniae* (strain 4074, approximately $10^7$ colony forming units). At the time of challenge, the control pigs were ear-tagged and blood was collected from four of these control pigs. Two days after challenge, all sixteen pigs were euthanized and necropsied.

A significant increase in the serum neutralizing antibody titer to the type 1 hemolysin of *A. pleuropneumoniae* occurred in the EM1-infected pigs as shown in the following Table. *A. pleuropneumoniae* complement fixation titers were negative both before and after exposure to the EM1 strain.

| Pig # | Bleed Date | CF[1] | HN[2] |
| --- | --- | --- | --- |
| 1 | Initial | Negative | 1483 |
|   | Post-Vaccination | Negative | 9537 |
| 2 | Initial | Negative | 1815 |
|   | Post-Vaccination | Negative | 4757 |
| 3 | Initial | Negative | 1761 |
|   | Post-Vaccination | Negative | 3108 |
| 4 | Initial | Negative | 1734 |
|   | Post-Vaccination | Negative | 5790 |
| 5 | Initial | Negative | 1634 |
|   | Post-Vaccination | Negative | 6329 |
| 6 | Initial | Negative | 2390 |
|   | Post-Vaccination | Negative | 6316 |
| 7 | Initial | Negative | 2452 |
|   | Post-Vaccination | Negative | 6007 |
| 8 | Initial | Negative | 3566 |
|   | Post-Vaccination | Negative | 8108 |

[1]Complement fixation titers against *A. pleuropneumoniae*
[2]Hemolysin neutralization titers against the type 1 hemolysin of *A. pleuropneumoniae*

Five out of eight (62%) of the control pigs developed severe clinical signs and correspondingly severe pneumonic lesions. It was judged that only one of the five pigs would have lived without aggressive treatment. Only one of eight (12%) of the EM1-infected pigs developed observable clinical signs of disease and it had mild lung lesions. The clinical signs and lung lesions in this pig were substantially less severe than the lesions in any of the control pigs. It was judged that this pig would have lived without therapy. At necropsy, pure cultures of *A. pleuropneumoniae* were isolated only from the pneumonic lesions of the control pigs. *A. suis* was not isolated.

It was thus concluded that inoculation with the EM1 strain of *A. suis* induced in the pigs sufficient RTX-neutralizing antibody titer to at least prevent clinical symptoms of pleuropneumonia in the test pigs, and in the majority of instances this inoculation also prevented infection of the pigs with *A. pleuropneumoniae*. The advantages of this type of immunization include a higher degree of protection than available with current vaccines, and the fact that the pigs are protected against vaccineinduced disease which might occur if the pigs were exposed to a live virulent strain of *A. pleuropneumoniae*.

*A. suis* and *A. pleuropneumoniae* are related but not identical organisms (e.g., different species in the same genus) The two species are easily differentiated on the basis of their growth characteristics, nutritional requirements, ability to ferment sugars, and specific DNA sequences. In addition, the diseases they may cause in pigs are typically very different. Recognized similarities between these organisms include some shared surface antigens as measured by serologic cross-reactivity and some of the toxins produced by certain strains of *A. suis*. This level of similarity is expected in organisms of the same genus but within each species, there can be significant degrees of strain variability.

EXAMPLE 2

In this example, methods for identification of vaccine strains of RTX toxin-secreting bacteria are described.

The vaccine strain should be gram-negative and should produce a clear zone of hemolysis when grown on sheep or cattle blood agar after incubation at 37° C. for not less than 24 hours and not more than 72 hours,.

When grown in liquid media, the bacterial vaccine strain should secrete hemolysin(s) (i.e. RTX-toxin(s)) into the media. For example, candidate strains of *A. suis* are grown in RPMU 1640 medium (Gibco Laboratories, Grand Island, N.Y.) supplemented with 2.5% fetal bovine serum and 0.023M sodium bicarbonate. Prior to inoculation of the growth medium with the bacteria, the media is filter-sterilized using 1 liter disposable filtration units which incorporate 0.02 $\mu$m cellulose acetate filters (Nalgene, a subsidiary of Sybron International, Rochester, N.Y.). Prior to filter sterilization, the pH of the media is adjusted to 7.25 to 7.30 with HCl.

Bacteria are grown in the receptacle portion of the media-filtration units until mid-log phase stage of growth. Bacterial growth occurs at 37° C. with moderate agitation (150–200 rpm) until the media turns from red to dark orange and optical density of the culture reaches 0.18 to 0.2 at 570 nm. When bacteria are in early log-phase growth, the culture supernatant will contain the most hemoltic activity on a per ml basis. Care should be taken to avoid having the culture grow beyond this point as the measurable hemolytic activity of the culture supernatant will be reduced significantly.

The bacterial cells are then removed from the media by centrifugation (3,500×g for 10 min) followed by filtration through disposable filtration units equipped with 0.02 $\mu$m nylon filters (Nalgene, a subsidiary of Sybron International, Rochester, N.Y.). The filtered culture supernatant is then aliquoted into 50 ml plastic disposable conical centrifuge tubes and frozen rapidly to −70° C. The hemolytic activity of the prepared culture supernatant is maintained for approximately 6 months when stored at −70° C.

The presence of hemolysin in the culture media supernatant is detected by its ability to lyse prepared sheep erythrocytes. Sheep erythrocytes are prepared from whole sheep blood (60 to 120 ml) collected by jugular venipuncture in heparin. The whole blood is mixed with 2 to 3 volumes of sterile physiologic saline in sterile plastic 50 ml conical centrifuge tubes and the erythrocytes pelleted by centrifugation at 700×g for 15 min at room temperature. The supernatant and buffy coat are removed and the remaining erythrocytes re-washed in 2 to 3 volumes of sterile saline, centrifuged, and the supernatant discarded. The washed erythrocytes are combined and re-suspended in citrate phosphate dextrose (CPD) solution (dextrose 1 mM, sodium citrate 0.9 mM, citric acid 0.16 mM, sodium phosphate-monobasic 0.1 6 mM; pH 5.6; osmolality of 280–300 mOsm/Kg) to a final packed cell volume of 10 to 15 percent. The erythrocyte packed cell volume is determined by the microhematocrit method as described by Coles (Veterinary Clinic Pathology, 4th edition, W. B. Saunders Company, Philadelphia), Prepared sheep erythrocytes are stored at 40° C. and are ready for use in the assay after being allowed to stabilize for 48 hr in the CPD. They can be maintained for at least two weeks by replacing the CPD with fresh CPD every 2 to 3 days.

A 1% suspension of sheep erythrocytes is prepared from the stock suspension of erythrocytes by the addition of 10 mM Tris/saline. The maximal releasable hemoglobin content of this suspension is determined by mixing 50 $\mu$l of the erythrocyte suspension with 150 $\mu$l of distilled water in the well of microtiter plates (Falcon 3910, Becton Dickinson Labware, Lincoln Park, N.J.). A standard curve of the hemolytic activity of the culture supernatant (FIG. 1: No Serum) is constructed by the addition of 0, 2, 5, 10, 20, 30, 50, 70, 90, and 100 $\mu$l of the prepared culture supernatant to wells of a round-bottom 96-well microtiter plates (Falcon 3910, Becton Dickinson Labware, Lincoln Park, N.J.) and the final volume of each well is adjusted to 100 $\mu$l with fresh RPMI 1640 medium. To all wells, 100 $\mu$l of a 1% erythrocyte suspension is added and the plates covered and incubated for 2 hr at 37° C. In order to pellet unlysed erythrocytes, the plates are then centrifuged at 120×g for 6 min. Then 100 $\mu$l of the supernatant from each well is transferred to a corresponding well of a flat-bottom microtiter plate (Immulon 3, Dynatech Laboratories, Inc., Chantilly, Va.) and any air-bubbles popped. The hemoglobin content of each well is then determined by measuring the optical density at 410 nm using a microplate reader (Vmax-microplate reader, Molecular Devices Corp., Sunnyvale, Calif.). All assays are completed in triplicate and the average value used in all subsequent calculations.

Changes in sheep erythrocyte volume, membrane fragility, and hemoglobin content are accounted for when the maximal hemoglobin release is determined by the addition of water. In addition, the data is normalized to the value of negative reference sera which are included in each assay. Typically, the maximal hemoglobin release produced by the addition of water to the sheep erythrocytes is only slightly higher than the maximal release caused by 100 $\mu$l of culture supernatant. If not, the results are discarded and the assay repeated using either new erythirocytes, new culture supernatant, or both.

A standard curve of hemolytic activity is developed based on quadratic evaluation of the data. The calculated variance of the standard curve should be 0.98 or better. If the variance is less than 0.90, the assay should be repeated. One hemolytic unit is defined as the number of $\mu$l of culture supernatant necessary to lyse 50% of 100 $\mu$l of a 1% suspension of sheep erythrocytes. The number of $\mu$l of culture supernatant composing one hemolytic unit is influenced by the hemolytic activity of the supernatant and the sensitivity of the erythrocytes. Vaccine strains should produce a culture supernatant in which 3 to 6 $\mu$l contains one hemolytic unit. When this value exceeds 10 $\mu$l of culture supernatant per hemolytic unit the strain is not considered further. As illustrated in FIG. 1 (No Serum), 5 $\mu$l of the culture supernatant produced by this strain equals one hemolytic unit.

Animals exposed to the vaccine bacterial strain should develop serum antibodies which neutralize the ability of the hemolysin to lyse sheep erythrocytes. To evaluate the ability of vaccine strains to induce RTX-neutralizing antibodies, serum from the test animal (e.g. pigs) is collected prior to and following exposure to the vaccine strain. The serum is evaluated for its ability to prevent lysis of erythrocytes by hemolytic culture supernatants (prepared as described above). At least a three-fold increase in hemolysin-neutralizing antibody titer should occur within three weeks after exposure to the vaccine strain.

To measure the hemolysin-neutralizing antibody titer, hemolytic culture supernatant of the A. pleuropneumoniae (0, 50, 75, and 100 μl) is added to round-bottom microtiter plate wells (Falcon 3910, Becton Dickinson Labware, Lincoln Park, N.J.) and the final volume of each well adjusted to 100 μl by the addition of fully supplemented RPMI 1640 medium. To each well, 5 μl of heat-inactivated (1 hr at 57° C.) test sera is added and the plate incubated for 1 hr at 37° C. To all well;, 100 μl of the 1% erythrocyte suspension is added and the plates covered and incubated for an additional 2 hr at 37° C. Neutralization titers are defined as the number of hemolytic units 1 ml of serum can neutralize.

The number of hemolytic units in the culture supernatant is calculated using the ELISA plate-reader software (Softmax, Molecular Devices Corp., Sunnyvale, Calif.). A quadratic equation is generated using the optical density of the supernatant from each well (proportional to the number of lysed erythrocytes) versus the μl of culture supernatant responsible for the lysis. A second standard curve in which 5 μl of test serum is added is then generated by the same method and the resulting shift in hemolytic activity calculated by determining the X-intercept at the 50% hemolysis point (FIG. 1).

Hemolysin-neutralizing antibody titers are calculated by dividing the number of μl of culture supernatant necessary to lyse 50% of the erythrocytes (e.g. one hemolytic unit) into the number of μl of culture supernatant necessary to cause the same degree of erythrocyte lysis when 5 μl of test serum is added. This value is multiplied by 200 to convert to hemolysin neutralizing activity per ml of serum.

For example, if 5 μl of culture supernatant contains one unit of hemolytic activity and a serum with low-neutralizing ability reduced this activity so it now takes 22 μl of the culture supernatant to lyse the same number of erythrocytes, the resulting hemolysin-neutralizing antibody titer for this serum is 880 (22/5×200). In contrast, for a serum with high-neutralizing ability it takes 386 μl of culture supernatant (by extrapolation) to lyse 50% of the erythrocytes; the hemolysin-neutralizing antibody titer is 15,400 (386/5×200) (FIG. 1).

Figure 2:
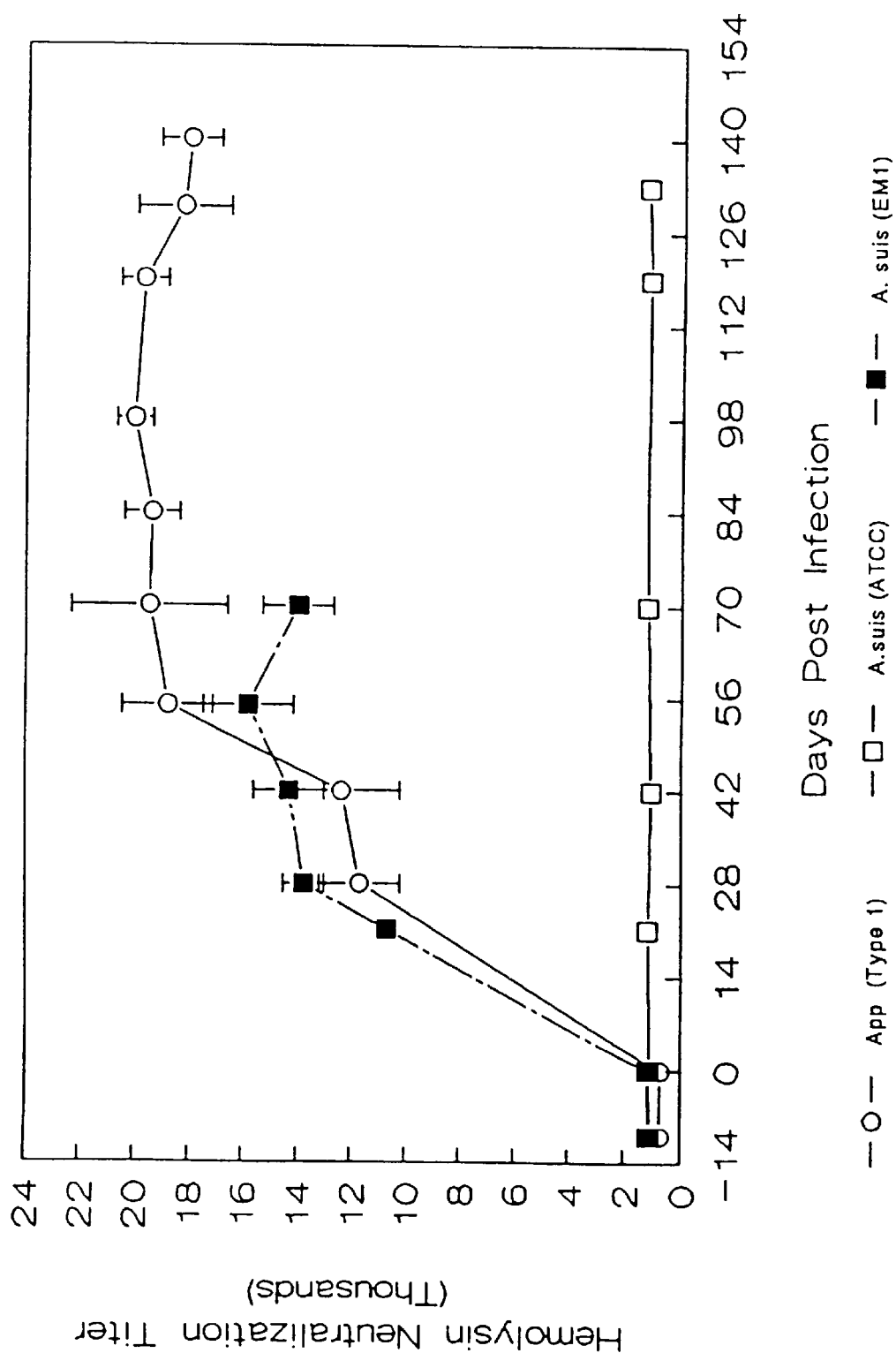
FIG. 2 depicts a graph illustrating changes in hemolysin-neutralizing antibody titers following exposure of pigs to *A. pleuropneumoniae* serotype 1 (n=12), *A. suis* strain ATCC (n=12), and *A. suis* strain EM1 (n=8)

FIG. 2 illustrates changes in hemolsin-neutralizing antibody titer over time in pigs following exposure to A. pleuropneumoniae (App) type 1 (circles, n=−12), A. suis strain ATCC (open squares, n=12), and A. suis strain EM1 (open squares, n=8). A. suis strain EM1 induces a marked increase in hemolysin-neutralizing antibody titer, and thus would be acceptable as a vaccine strain. In contrast, A. suis strain ATCC does not induce a hemolysin-neutralizing antibody titer and thus, would not meet this criteria.

Figure 3:
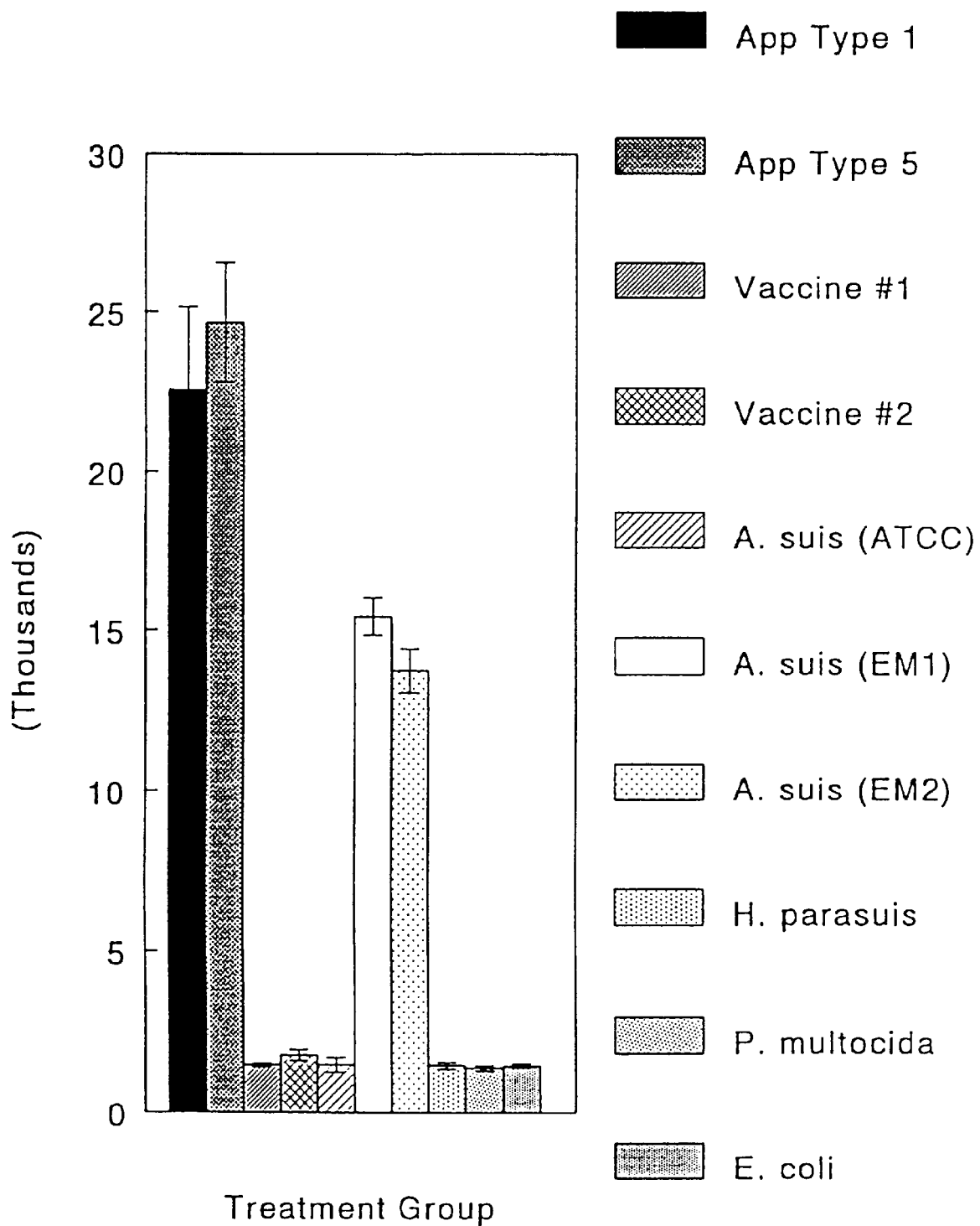
FIG. 3 depicts a graph illustrating peak hemolysin-neutralizing antibody titers in pigs following either exposure to various bacteria or vaccination with commercial vaccines.

FIG. 3 illustrates hemolysin-neutralizing antibody titers of groups of pigs six weeks after exposure to A. pleuropneumoniae (App) types 1 or 5, after vaccination with commercial vaccines (vaccine #1 and #2), or after exposure to various bacteria. Only infection with A. pleuropneumoniae serotypes 1 or 5, or A. suis strain EM1 induces a significant increase in hemolysin-neutralizing antibody titer.

Taken together, FIGS. 2 and 3 demonstrate that some but not all bacteria have the ability to induce neutralizing antibodies to the RTX toxins produced by other bacteria. In a similar fashion, commercial vaccines fail to induce IRTX-neutralizing antibody titers.

Animals exposed to the vaccine strain should not develop severe clinical signs, but should be protected from clinical disease following subsequent exposure to pathogenic bacteria. It is clear from numerous studies that exposure to A. pleuropneumoniae induces high hemolysin-neutralizing antibody titers and immunity against disease following subsequent exposure to this same organism (convalescent immunity). Unfortunately, this strain as well as many others are pathogenic and can cause clinical disease which makes them unacceptable as vaccine strains. A vaccine strain of this organism or a related organism should induce a high hemolysin-neutralizing antibody titer but not cause significant clinical disease.

A. suis strains EM1, EM2, and ATCC were screened for their ability to induce a high RTX-neutralizing antibody titer without causing significant clinical disease using the procedure described above. Groups of pigs were experimentally inoculated intranasally with approximately $5 \times 10^7$ viable cells of either A. suis strains EM1, EM2, or ATCC, or A. pleuropneumoniae serotype 1 or 5. Serum samples were collected prior to and 5 weeks post-inoculation and the serum hemolysin neutralization determined. The data illustrated in FIG. 4 demonstrate that significant neutralization titers are induced as a consequence of exposure to either A. suis strain EM1 or EM2, or A. pleuropneumoniae serotypes 1 or 5. In contrast, exposure to A. suis strain ATCC failed to have the same effect.

In addition, pigs were exposed to either A. suis strain EM1, EM2, or ATCC, then challenged with A. pleuropneumoniae. Pigs exposed to A. suis strain EM1 were challenged with A. pleuropneumoniae serotype 1 (as described in Example 1), while pigs exposed to A. suis strain EM2 were challenged with A. pleuropneumoniae serotype 5.

Figure 4:
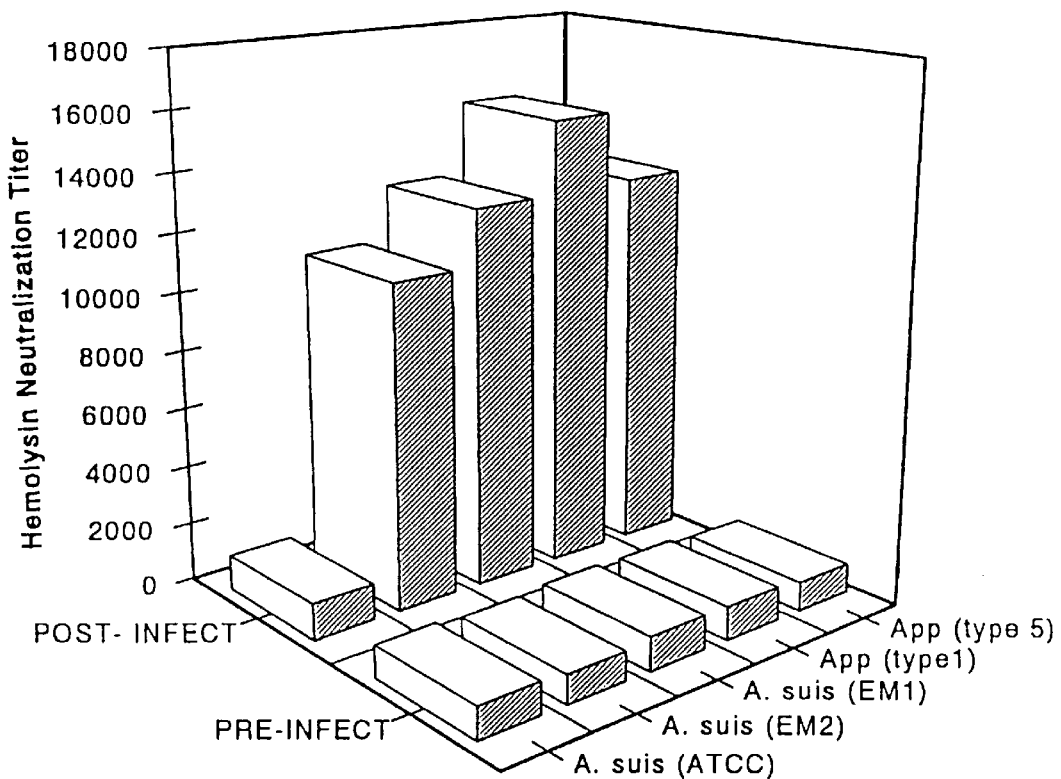
FIG. 4 depicts a graph illustrating the ability of *A. suis* strains EM1 and EM2, and *A. pleuropneumoniae* serotypes 1 and 5, but not *A. suis* strain ATCC to induce serum hemolysin-neutralizing antibody titers following experimental infection.
Figure 5:
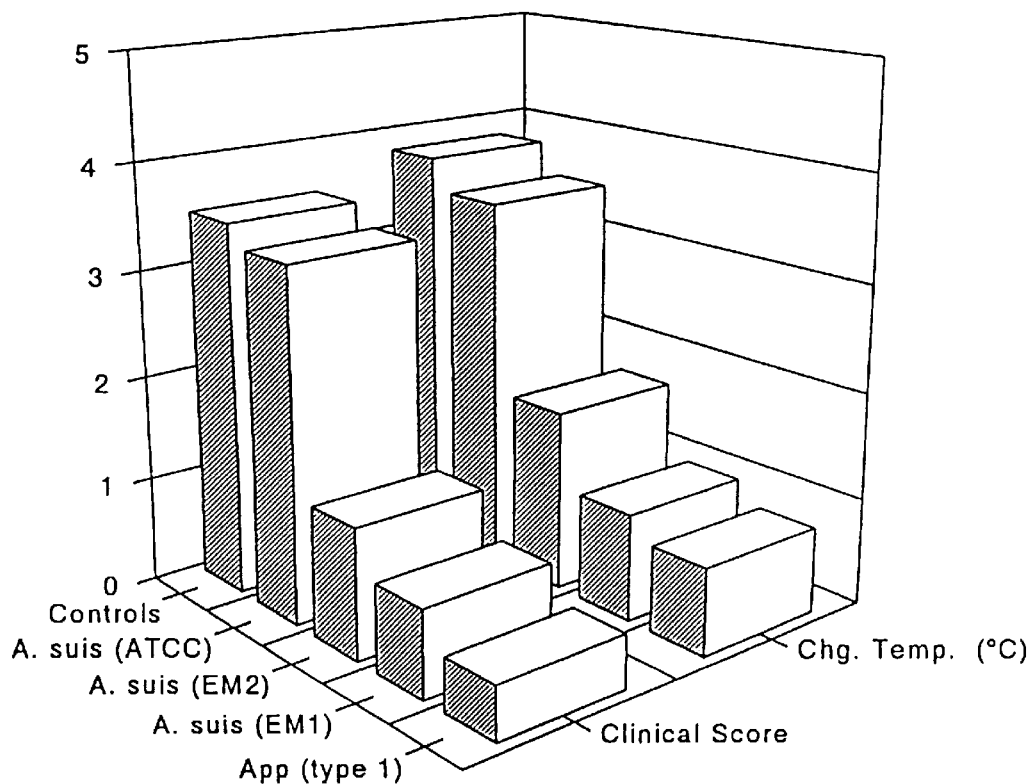
FIG. 5 depicts a graph illustrating the ability of *A. suis* strains EM1 and EM2, and *A. pleuropneumoniae* serotype 1, but not *A. suis* strain ATCC to provide protection from disease as measured by clinical score and change in temperature after being challenged with *A. pleuropneumoniae*; the datca represent the average clinical score for each group as graded on a scale of 0 to 4 and average change in temperature 24 hours after being challenged with *A. pleuropneumoniae*.

Pigs inoculated with A. suis strain EM2 had a mild reaction (increased temperature, sneezing, anorexia) which lasted not longer than 24 hours. As a result of this inoculation, hemolysin-neutralizing antibody titers increased significantly (FIG. 4). When challenged with virulent A. pleuropneumoniae serotype 5, these pigs were protected from clinical disease (FIG. 5) and pneumonia. In contrast, pigs exposed to A. suis strain ATCC did not develop significant hemolysin-neutralizing antibody titers (FIG. 4) and were not protected from disease when exposed to A. pleuropneumoniae (FIG. 5).

Pigs or other animals exposed to strains of bacteria that induce a high RTX-neutralizing antibody titer without causing significant clinical disease as demonstrated by the procedures described above (e.g. A. suis strains EM1 and EM2) are provided a degree of immunity from clinical disease associated with infection with more virulent bacteria which produce related toxins (e.g. A. pleuropneumoniae serotypes 1 or 5). Exposure to the vaccine strains could be by intranasal or oral inoculation, parenteral injection, or environmental seeding (e.g. water, food, foggy, misting, etc.). The routine, duration, amount, and frequency of the exposure would be such that serum hemolysin neutralization titers are induced. For example, not more than approximately $5 \times 10^7$ viable cells of A. suis strain EM1 or EM2 are necessary to have this effect when used to inoculate pigs intranasally. More or less viable cells might be required to have the same effect when other strains of bacteria or other routines of administration are utilized.

A sample of A suis strain EM2 has been deposited with the AmericanType Culture Collection, Rockville, Md., and has been accorded Accession No. 55711.

I claim:

1. A method of immunizing swine against an infectious disease caused by bacteria which secrete RTX toxins, said method comprising the step of administering to said swine an effective amount of a live, immunizing, RTX toxin-secreting organism belonging to a species which is different than the species of said bacteria for inducing in the swine a RTX toxin-neutralizing antibody titer to at least prevent clinical symptoms of said disease in said swine, said organism being gram negative and being further identifiable by a procedure comprising the steps of:

(a) providing RPMI 1640 medium supplemented with 2.5% fetal bovine serum and 0.023M sodium bicarbonate, wherein the medium is filter-sterilized using 1 liter disposable filtration units incorporating 0.02 μm cellulose acetate filters and the pH of the medium is adjusted to 7.25–7.30 with hydrochloric acid;

(b) inoculating the medium with the organism and growing the organism at 37° C. with moderate agitation to generate a supernatant and until the medium turns from red to dark orange and the optical density of the culture reaches 0.18 to 0.2 at 570 nm;

(c) separating said supernatant;

(d) contacting the supernatant with sheep erythrocytes and determining if 3–6 μl of the supernatant is capable of lysing 50% of 100 μl of a 1% suspension of the sheep erythrocytes;

(e) if the organism passes step (d), intranasally exposing swine to the organism, and collecting blood samples from the swine prior to and following exposure to the organism; and (f) exposing swine to said organism and determining whether the swine generate RTX-neutralizing antibody titers without developing clinical symptoms of the disease.

2. The method of claim 1, said organism being selected from the group consisting of gram-negative bacteria of the genera Actinobacillus, Pasteurella, Haemophilus, Escherichia and Salmonella.

3. The method of claim 2, said organism being *Actinobacillus suis*.

4. The method of claim 3, said organism being the EM1 or EM2 strain of *Actinobacillus suis*.

5. The method of claim 1, including the step of parenterally administering said organism.

6. The method of claim 1, including the step of intranasally administering said organism.

7. The method of claim 1, said disease being selected from the group consisting of pleuropneumonia, pneumonia, enteritise, septicemia and rhinitis.

8. A vaccine for immunizing swine against diseases caused by bacteria which secrete RTX toxins, said vaccine comprising an effective amount of a live, immunizing, RTX toxin-secreting organism belonging to a species which is different than the species of said bacteria which when administered to swine induces at RTX toxin-neutralizing antibody titer in said swine to at least prevent clinical symptoms of said disease, said immunizing organism being in a pharmaceutically acceptable carrier which will support viability of said strain and said organism being gram negative and being further identifiable by a procedure comprising the steps of:

(a) providing RPMI 1640 medium supplemented with 2.5% fetal bovine serum and 0.023M sodium bicarbonate, wherein the medium is filter-sterilized using 1 liter disposable filtration units incorporating 0.02 μm cellulose acetate filters and the pH of the medium is adjusted to 7.25–7.30 with hydrochloric acid;

(b) inoculating the medium with the organism and growing the organism at 37° C. with moderate agitation to generate a supernatant and until the medium turns from red to dark orange and the optical density of the culture reaches 0.18 to 0.2 at 570 nm;

(c) separating said supernatant;

(d) contacting the supernatant with sheep erythrocytes and determining if 3–6 μl of the supernatant is capable of lysing 50% of 100 μl of a 1% suspension of the sheep erythrocytes;

(e) if the organism passes step (d), intranasally exposing swine to the organism, and collecting blood samples from the swine prior to and following exposure to the organism; and (f) exposing swine to said organism and determining whether the swine generate RTX-neutralizing antibody titers without developing clinical symptoms of the disease.

9. The vaccine of claim 8, said organism being selected from the group consisting of gram-negative bacteria of the genera Actinobacillus, Pasteurella, Haemophilus, Escherichia and Salmonella.

10. The vaccine of claim 9, said organism being *Actinobacillus suis*.

11. The vaccine of claim 10, said organism being the EM1 EM2 strain of *Actinobacillus suis*.

12. A method of immunizing swine against porcine pleuropneumonia comprising the step of parenterally administering to said swine an effective amount of a strain of *A. suis* capable of inducing in the swine a RTX toxin-neultralizing antibody titer to at least prevent clinical symptoms of porcine pleuropneumonia in said swine.

13. A vaccine for immunizing swine against porcine pleuropneumonia comprising an effective amount of a live strain of *A. suis* which when administered to swine induces a RTX toxin-neutralizing antibody titer in said swine to at least prevent clinical symptoms of porcine pleuropneumonia, said strain being in a pharmaceutically acceptable carrier which will support viability of said strain.

* * * * *